US010279531B2

(12) United States Patent
Pagliarini

(10) Patent No.: US 10,279,531 B2
(45) Date of Patent: May 7, 2019

(54) MOULDING DEVICE FOR MOULDING A CONTAINER STARTING WITH A PARISON IN PLASTIC MATERIAL AND MOULDING MACHINE COMPRISING THIS DEVICE

(71) Applicant: GEA PROCOMAC S.P.A., Sala Baganza (IT)

(72) Inventor: Paolo Pagliarini, Parma (IT)

(73) Assignee: GEA PROCOMAC S.P.A., Sala Baganza (IT)

(*) Notice: Subject to any disclaimer, the term of this patent is extended or adjusted under 35 U.S.C. 154(b) by 45 days.

(21) Appl. No.: 15/327,246

(22) PCT Filed: Jun. 26, 2015

(86) PCT No.: PCT/IB2015/054838
§ 371 (c)(1),
(2) Date: Jan. 18, 2017

(87) PCT Pub. No.: WO2016/012883
PCT Pub. Date: Jan. 28, 2016

(65) Prior Publication Data
US 2017/0173844 A1   Jun. 22, 2017

(30) Foreign Application Priority Data

Jul. 21, 2014  (IT) .............................. PR2014A0049

(51) Int. Cl.
B29C 49/46    (2006.01)
B29C 49/06    (2006.01)
(Continued)

(52) U.S. Cl.
CPC .............. B29C 49/46 (2013.01); B29C 49/06 (2013.01); A61L 2/14 (2013.01); A61L 2202/23 (2013.01); B29C 49/12 (2013.01)

(58) Field of Classification Search
CPC .......... B29C 49/46; B29C 46/06; B29C 49/12
See application file for complete search history.

(56) References Cited

U.S. PATENT DOCUMENTS 4,265,730 A * 5/1981 Hirose .................... B29C 59/14
                                                            118/723 AN
5,236,636 A * 8/1993 Tisack ................ B29C 45/0053
                                                            264/102
(Continued)

FOREIGN PATENT DOCUMENTS

DE   10 2011 016 448 A1   4/2012
DE   10 2011 075 171 A1   8/2012
(Continued)

Primary Examiner — Yogendra N Gupta
Assistant Examiner — Emmanuel S Luk
(74) Attorney, Agent, or Firm — Jeffrey N. Townes; Cozen O'Connor

(57) ABSTRACT

Molding device (1) for molding a container starting with a parison (3) in plastic material, comprising: two half-molds (4a, 4b), which may be joined to define at least one housing cavity (5) for the parison (3); a blowing nozzle (6) applicable on the neck (3b) of the parison (3); a plasma generator (8) receiving a blowing fluid at a pressure higher than the atmospheric pressure and supplying plasma at a pressure higher than the atmospheric pressure to the blowing nozzle (6), so that the plasma is blown into the parison (3) placed in the housing cavity (5) to mold it and to decontaminate it.

5 Claims, 2 Drawing Sheets

(51) Int. Cl.
*B29C 49/12* (2006.01)
*A61L 2/14* (2006.01)

(56) References Cited

U.S. PATENT DOCUMENTS

| | | | | |
|---|---|---|---|---|
| 5,378,510 A | * | 1/1995 | Thomas | B05D 1/62 215/12.2 |
| 5,521,351 A | * | 5/1996 | Mahoney | B23K 10/027 118/723 R |
| 6,054,016 A | * | 4/2000 | Tuda | H01J 37/32192 118/723 MR |
| 6,109,208 A | * | 8/2000 | Tsuchihashi | H01J 37/3222 118/723 MA |
| 6,117,243 A | * | 9/2000 | Walther | C03C 17/004 118/712 |
| 6,565,791 B1 | * | 5/2003 | Laurent | A61L 2/14 264/129 |
| 7,244,381 B2 | * | 7/2007 | Chatard | B05D 1/60 264/84 |
| 7,638,727 B2 | * | 12/2009 | Kumar | B01J 19/088 118/723 MW |
| 7,744,790 B2 | * | 6/2010 | Behle | B05D 1/62 264/328.1 |
| 7,754,302 B2 | * | 7/2010 | Yamasaki | B65D 1/0215 220/62.12 |
| 7,985,188 B2 | * | 7/2011 | Felts | B05D 1/62 427/488 |
| 9,272,095 B2 | * | 3/2016 | Felts | A61M 5/3129 |
| 9,664,626 B2 | * | 5/2017 | Fisk | C23C 16/04 |
| 9,764,093 B2 | * | 9/2017 | Weikart | A61M 5/3129 |
| 2002/0176947 A1 | * | 11/2002 | Darras | B05D 1/62 427/569 |
| 2003/0219547 A1 | * | 11/2003 | Arnold | B08B 7/00 427/569 |
| 2006/0110483 A1 | * | 5/2006 | Damerow | B29C 49/4268 425/1 |
| 2007/0281108 A1 | * | 12/2007 | Weikart | C08J 7/123 427/575 |
| 2008/0017113 A1 | * | 1/2008 | Goto | C23C 16/045 118/723 R |
| 2008/0258353 A1 | * | 10/2008 | Hutchinson | B29C 45/1618 264/483 |
| 2010/0193461 A1 | * | 8/2010 | Boutroy | B05D 1/62 215/12.2 |
| 2012/0061883 A1 | | 3/2012 | Gottlieb et al. | |
| 2014/0015171 A1 | * | 1/2014 | Herold | A61L 2/14 264/483 |
| 2015/0367555 A1 | * | 12/2015 | Winzinger | B29C 49/36 198/339.1 |
| 2016/0052177 A1 | * | 2/2016 | Chauvin | B29C 49/12 264/524 |

FOREIGN PATENT DOCUMENTS

EP 2431409 A1 9/2010
WO 2012/130197 A1 10/2012

* cited by examiner

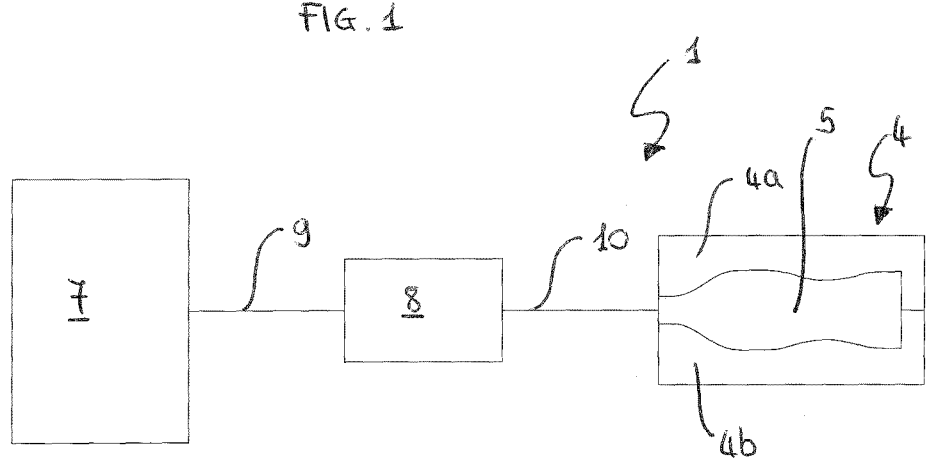
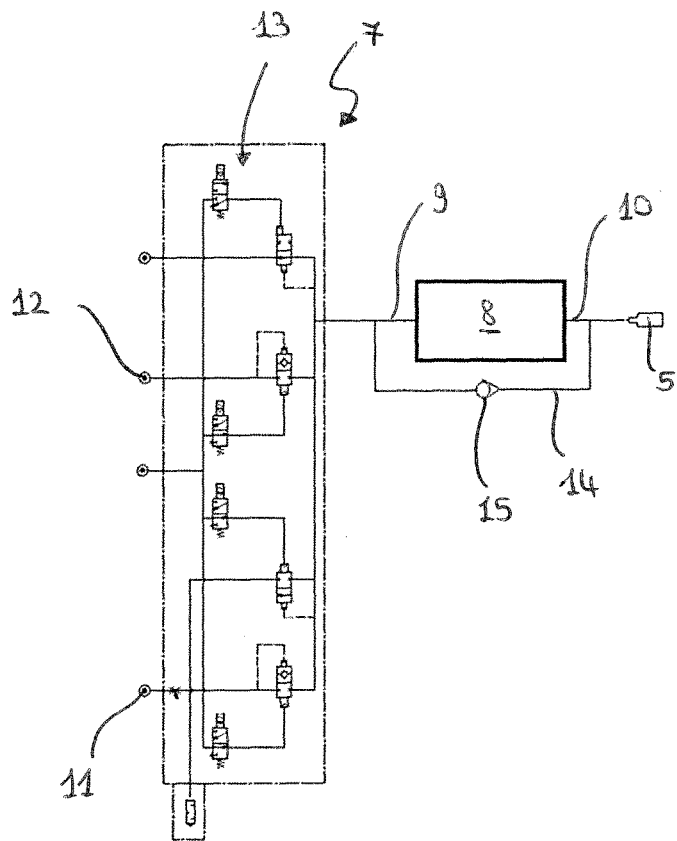

MOULDING DEVICE FOR MOULDING A CONTAINER STARTING WITH A PARISON IN PLASTIC MATERIAL AND MOULDING MACHINE COMPRISING THIS DEVICE

CROSS-REFERENCE TO RELATED APPLICATIONS

This application is a national-stage application under 35 U.S.C. § 371 of PCT Application No. PCT/IB2015/054838, filed Jun. 26, 2015, which claims priority to Italian Patent Application No. PR2014A000049, filed Jul. 21, 2014, which are hereby incorporated by reference in their entirety.

TECHNICAL FIELD

The object of the present invention is a moulding device for moulding a container starting with a parison in plastic material and a moulding machine comprising this device.

The reference sector is the bottling of so-called "sensitive" food products, i.e. products that are particularly sensitive to bacteriological contamination and oxidation, such as, for example, isotonic drinks, juices, nectars, soft drinks, tea, milk-based drinks, coffee-based drinks, etc., for which the prevention of possible microbiological contamination throughout all packaging stages is of fundamental importance.

STATE OF THE ART

Packaging lines using aseptic technology are already known, wherein the various operations take place in a controlled contamination environment, so that the bottled products can be stored for a prolonged period of time and have chemical/physical and organoleptic stability even at room temperature.

Aside from differences in design, a "conventional" aseptic bottling line envisages:
moulding the container starting with a parison made of a thermoplastic material;
chemical sterilisation of the moulded container;
rinsing, filling and capping of the filled container, to be carried out in a sterile environment.

The main drawback of conventional lines is related to the need to have to sterilise the container once it has been moulded and to maintain the sterilised state thereof throughout all subsequent operations, for example the filling and capping operations.

A modern concept of an aseptic bottling line instead envisages:
sterilisation of the parison using chemical agents or radiation sterilisation;
"aseptic" moulding of the container starting with a parison made of a thermoplastic material;
filling and capping of the filled container, to be carried out in a sterile environment.

In this regard, the Applicant has developed a moulding apparatus for moulding under aseptic conditions, in which the moulding rotary carousel is protected by an isolation device suitable for defining a controlled-contamination environment, and the movement means for moving the carousel and moulds is located outside of said isolation device (see European Patent EP2246176).

The preliminary sterilisation stage involves all devices that come into contact with the parison subjected to moulding by blowing and stretching, including for example the gripping members, the stretching rod and the blown air circuit. The Applicant has thus developed ad hoc solutions for the stretching rod (see European Patent no. EP 2340157) and for the blown air circuit (European patent application no. EP 26443142).

In this manner, the Applicant has reached the point of developing a completely aseptic blow moulding machine, characterised by evident structural complexity.

It should also be added that not all the manual procedures required during operation (e.g. removal of obstacles) can be performed with the use of handling gloves. In some cases, it may be necessary to open the isolator access door, resulting in the loss of sterile conditions. Upon completion of the procedure, the sterile conditions of the environment must be restored, resulting in an evident loss of time due to downtime of the line.

Aside from sterilisation using chemical agents or radiation sterilisation, the use of plasma for the sterilisation of objects has been adopted for several decades, for example in the medical field.

The plasma is obtained by passing a gas or a gas mixture (e.g. air or oxygen) between two electrodes between which an electrical discharge is generated, so that ionized particles are formed. Since the first plasma generators, which comprised a vacuum chamber, technology has evolved towards the generation of atmospheric pressure plasma. For example, patent no. WO 2007/071720 refers to a method for the sterilisation of objects by means of plasma generated at atmospheric pressure.

The principal advantages associated with the use of plasma for sterilisation consist of:
treatment of objects of any shape and material;
rapidity of the treatment;
safety of the process, owing to the low temperatures involved and the absence of chemical agents.

Plasma sterilisation has thus spread to diverse industrial sectors, among which the bottling sector as well.

For example, patent no. WO 2009/101156 proposes the treatment of HEPA containers and filters using plasma.

Patent no. WO99/17334 discloses the use of plasma for sterilising the inside of bottles.

Patent no. EP 2182991 discloses an apparatus and method for sterilising parisons made of a plastic material using plasma. It is specified that in a first embodiment the sterilisation treatment uses plasma at ambient pressure, whereas in a second embodiment the plasma treatment is carried out at a pressure higher than ambient pressure. In all of the embodiments described, the plasma generator is located along the transport path of the parisons, upstream of the blowing device, and therefore sterilisation takes place prior to the blowing phase.

Patent no. WO 2012/130197 also describes the use of plasma for sterilising parisons made of plastic material. In this solution, the plasma generator is located at the blowing station. In particular, the plasma is generated at atmospheric pressure outside of the parison and then inserted therein by means of a nozzle placed in the stretching rod.

If one wishes to use plasma to decontaminate parisons or containers on an aseptic bottling line, one is in any case always faced with the problem of having to manage the interface separating the controlled-contamination environment and the contaminated external environment.

In this context, the basic technical task of the present invention is to offer a moulding device for moulding a container starting with a parison in plastic material, as well as a moulding machine comprising this device, both of which overcoming the drawbacks of the prior art mentioned hereinabove.

AIM OF THE INVENTION

In particular, an aim of the present invention is to make available a device and a machine for moulding a container starting with a parison in plastic material, both the device and the machine being structurally simpler compared to the prior-art solutions.

The defined technical task and the specified aims are substantially achieved by a moulding device for moulding a container starting with a parison in plastic material and by a moulding machine, comprising:

two half-moulds, which may be joined to define at least one housing cavity for the parison;

supply means for supplying a blowing fluid having a pressure higher than the atmospheric pressure;

a blowing nozzle applicable on the neck of said parison;

a plasma generator having an inlet receiving the blowing fluid from said supply means and an outlet enabled to supply plasma at pressure higher than the atmospheric pressure to said blowing nozzle, so that said plasma is blown into the parison placed in said housing cavity to mould it at least partially and to decontaminate it.

In this context, the term decontamination is used in a broad sense to indicate a reduction in the number of microorganisms, as well as the killing of all microorganisms (which involves actual sterilisation).

BRIEF DESCRIPTION OF THE DRAWINGS

Further characteristics and advantages of the present invention will become more apparent from the approximate and thus non-limiting description of a preferred, but not exclusive, embodiment of a moulding device for moulding a container starting with a parison in plastic material, and a moulding machine comprising this device, as illustrated in the accompanying drawings, of which:

FIG. 1 is a block diagram of a moulding device for moulding a container starting with a parison in plastic material, according to the present invention;

FIG. 2 is a block diagram of a first embodiment of the moulding device of FIG. 1, with a detail of the circuit of the supply means supplying the blowing fluid;

DETAILED DESCRIPTION OF PREFERRED EMBODIMENTS OF THE INVENTION

Figure 3:
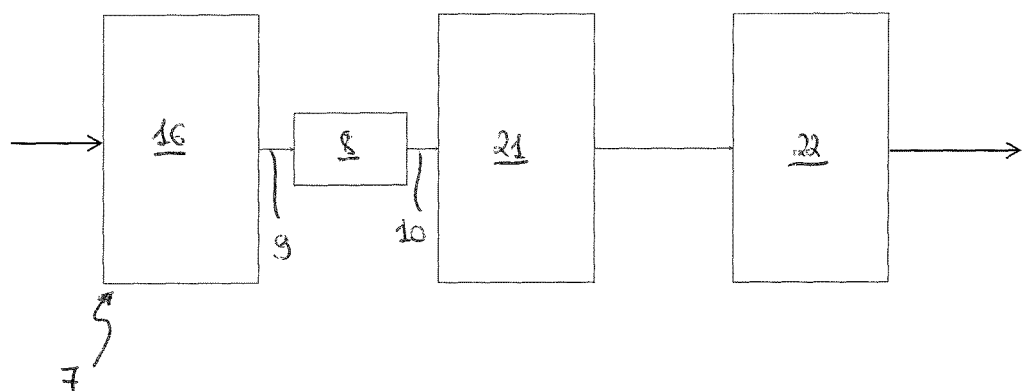
FIG. 3 is a partial block diagram of a second embodiment of the moulding device of FIG. 1.

With reference to the figures, a moulding device for moulding a container starting with a parison 3 in plastic material, for example PET, is indicated by the number 1.

The parison 3 has a tubular body 3a and a neck 3b that does not undergo the moulding process.

The moulding device 1 comprises two half-moulds 4a, 4b that can be joined to define at least one housing cavity 5 for the parison 3.

A blowing nozzle 6 or seal can be applied on the neck 3b of the parison 3. The moulding device 1 comprises supply means 7 for supplying a blowing fluid having a pressure higher than the atmospheric pressure. For example, the fluid can consist of air.

Originally, the moulding device 1 comprises a plasma generator 8 that has an inlet 9 receiving the blowing fluid from the supply means 7 and an outlet 10 enabled to supply plasma at a pressure higher than the atmospheric pressure to the blowing nozzle 6, so that the plasma is blown into the parison 3 that is found in the housing cavity 5. Subjected to blowing with the plasma, the parison 3 is thus moulded and decontaminated.

The plasma moulding can take place partially, that is, by sending plasma at a maximum pressure of about 16 bar (pre-blowing phase) or by sending plasma until the moulding is completed (pre-blowing phase and the actual blowing phase).

The two half-moulds 4a, 4b are preferably part of a mould 4 that also comprises a bottom plate (unillustrated) positioned on one of the bases of the mould 4.

In a first embodiment, which is illustrated in FIG. 2, the fluid supply means 7 comprise:

a primary line 11 enabled to transport blowing fluid at a maximum pressure of around 16 bar;

a secondary line 12 enabled to transport blowing fluid at a maximum pressure of around 40 bar;

a valve unit 13 configured to place the primary line 11 and the secondary line 12 in selective communication with the inlet 9 of the plasma generator 8.

In the first embodiment, the plasma generator 8 is interposed between the valve unit 13 and the blowing nozzle 6.

The plasma generator 8 is preferably positioned near the blowing nozzle 6.

Alternatively, the plasma generator 8 is integrated in the valve unit 13.

A discharge line 14 also shown in FIG. 2 is enabled to set the valve unit 13 in communication with the housing cavity 5. This discharge line 14 is provided with a non-return valve 15 and it is placed in parallel with the plasma generator 8 to evacuate residual gas quickly from the inside of the container once the moulding of the latter is completed.

The plasma generator 8 does not in itself represent the object of the present invention. However, it should be noted that in the first embodiment, the structural design chosen for the plasma generator 8 must be capable of operation with inlet pressures of up to 40 bar (in fact, the blowing fluid coming from the secondary line 12 reaches these pressure levels).

It is a known fact that an increase in the pressure of the incoming fluid makes it more difficult to activate the plasma because it increases the resistance of the fluid (which functions as a dielectric) to the discharge. Therefore, the voltage to be applied between the electrodes to activate high inlet pressures would even be in the range of about 20-30 kV.

To meet the need for operation with pressures of about 40 bar, a plasma torch (or gun) can be employed as a plasma generator 8; the torch supplies as output a direct flow of plasma from a nozzle. In particular, the plasma generator 8 consists in the plasma torch described in document DE 10115241.

In this torch, the plasma is activated at a pressure lower than the initial inlet pressure, owing to the presence of a convergent element. Subsequently, the pressure is brought back to its initial level by means of a divergent element. Through the use of this torch in the first embodiment, the plasma can be activated at pressures within the range of 6-8 bar even in the presence of an inlet blowing fluid in the range of about 30-40 bar.

An automatic system of the "mobile plug" type can the integrated in the plasma torch of document DE 10115241 with the aim of adapting it to the pressure level of the incoming fluid. This system changes the geometry of the elements from convergent to divergent and vice versa. In this manner, the plasma is generated independently of the inlet fluid pressure level. Moreover, the torch disclosed in document DE 10115241 has an added inlet for an additional fluid (for example water vapour or nitrogen) for the purpose of modifying the characteristics of the plasma to make it suitable for use in blowing the parison 3.

In a second embodiment, which is illustrated in FIG. 3, the fluid supply means 7 comprise:
- at least one compression stage 16 for the fluid, enabled to generate the blowing fluid;
- a plasma distribution circuit, which receives the plasma (directly or indirectly) from the outlet 10 of the plasma generator 8, and which, in turn, comprises a primary line to transport plasma having a maximum pressure of around 16 bar and a secondary line to transport plasma having a maximum pressure of around 40 bar;
- a valve unit configured to place the primary line and the secondary line in selective communication with the blowing nozzle 6.

In the second embodiment, the compression stage 16 for the fluid is placed upstream of the plasma generator 8.

For example, there is a single compression stage 16 and it generates blowing fluid having a maximum pressure of about 40 bar. As an alternative, there may be a number of compression stages in a cascade arrangement that are able to generate blowing fluid having a maximum pressure of about 40 bar. As the production of plasma takes place with the pressures of about 40 bar, the plasma distribution circuit receives the plasma directly from the outlet 10 of the plasma generator 8.

Given the high pressure of the blowing fluid supplied at the inlet 9 of the plasma generator 8, the torch disclosed in document DE 10115241, integrated with a mobile plug, can be employed as the plasma generator 8 in this second embodiment as well.

In a preferred variant, the compression stage 16 generates blowing fluid having a pressure of about 8 bar. In this case, it is sufficient to employ a plasma generator capable of operating with relatively low inlet pressures.

In this preferred variant, one or more plasma compression stages 21, 22 are present downstream of the plasma generator 8 and they receive the plasma from the outlet 10 of the plasma generator 8 and compress it to a maximum pressure of about 40 bar.

For example, two plasma compression stages 21, 22 are illustrated in FIG. 3 in a cascade arrangement:
- a first stage 21 capable of compressing the plasma up to a maximum pressure of about 20 bar;
- a second stage 22 capable of compressing the plasma up to a maximum pressure of about 40 bar.

In this preferred variant, the plasma distribution circuit receives the plasma indirectly from the outlet 10 of the plasma generator 8, that is, passing through the first stage 21 and the second stage.

Figure 4:
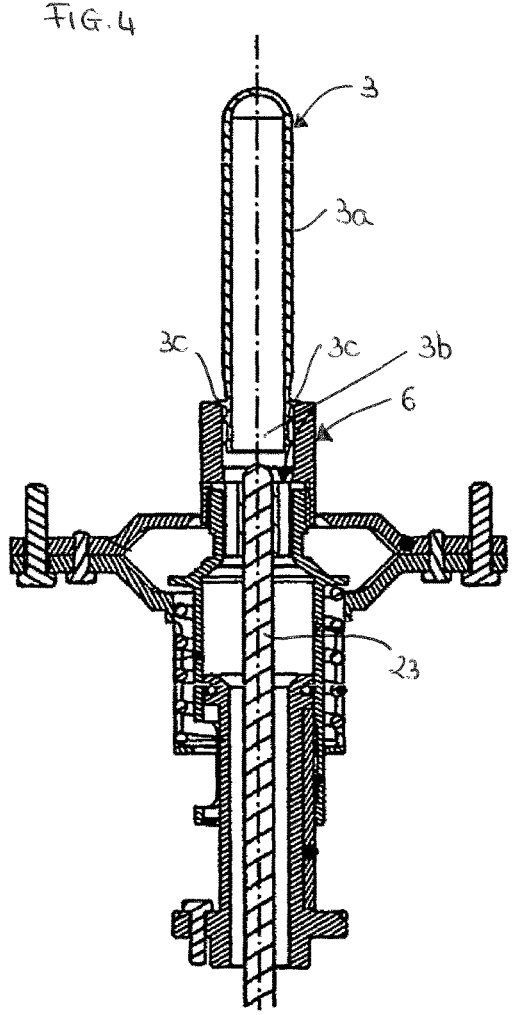
FIG. 4 is a sectional view of a detail of the device of FIG. 1, that is, the area of the blowing nozzle that is applied on the neck of a parison.

FIG. 4 shows the area of the blowing nozzle 6 applied on the neck 3*b* of the parison 3. In particular, the blowing nozzle 6 creates a tight seal on a transverse protrusion 3*c* (known in the field by the technical term "bague") of the neck 3*b* of the parison 3 in such a manner as to close the opening of the parison 3 in a tightly sealed manner during the moulding process.

The moulding machine (unillustrated) proposed herein comprises a plurality of moulding devices 1 described hereinabove. The moulding machine is preferably of the rotary carousel type. Alternatively, the moulding machine may be of the linear type.

The operation of the moulding device for moulding a container starting with a parison in plastic material is explained below.

First of all, the mould 4 must be arranged in an open configuration. This is done by moving the two half-moulds 4*a*, 4*b* away from each other so as to enable insertion of the parison 3 in the mould 4.

The mould 4 is subsequently brought into a closed configuration, joining the two half-moulds 4*a*, 4*b* in such a manner that they define, together with the bottom plate, the housing cavity 5 for the parison 3.

The moulding of the parison 3 by blowing takes place by blowing a plasma having a pressure higher than the atmospheric pressure into the parison 3. As plasma is used rather than a blowing fluid, the parison 3 is also decontaminated.

In particular, the blow moulding process comprises:
- pre-blowing, in which the plasma is blown into the parison 3 at a maximum pressure of about 16 bar;
- actual blowing, following the pre-blowing phase, and in which the plasma is blown into the parison 3 at a maximum pressure of about 40 bar.

In the first embodiment, the generation of plasma takes place near the mould 4 starting with the blowing fluid coming from the valve unit 13.

In particular, during the pre-blowing phase, the valve unit 13 enables communication of the inlet 9 of the plasma generator 8 with the primary line 11 bearing the fluid at the maximum pressure of about 16 bar.

During the actual blowing phase, the valve unit 13 enables communication of the inlet 9 of the plasma generator 8 with the secondary line 12 bearing the fluid at the maximum pressure of about 40 bar.

At the end of the moulding process, the residual gas remaining inside the container is evacuated through the discharge line 14.

In the second embodiment, the generation of plasma takes place downstream of the blowing fluid compression stage 16.

In particular, in the preferred variant of the second embodiment, the compression stage 16 generates the blowing fluid having a maximum pressure of about 8 bar, a fluid that is converted into plasma by the plasma generator 8. This plasma is then further compressed in the two plasma compression stages 21, 22 up to about 40 bar.

During the pre-blowing phase, the valve unit enables communication of the primary line bearing the plasma at a maximum pressure of about 16 bar with the blowing nozzle 6.

Continuing to blow plasma is also possible during the actual blowing phase, setting the secondary line, which bears the plasma at the maximum pressure of about 40 bar, in communication with the blowing nozzle 6.

The presence of a stretching rod 23 is preferably comprised in all the embodiments described herein. In particular, during the pre-blowing phase, the blowing nozzle 6 creates a tight seal on the bague 3*c* so as to close the mouth of the parison 3 in a tightly sealed manner. The stretching rod 23 is gradually inserted inside the tubular body 3*a* of the parison 3 until it reaches the bottom thereof. After touching the bottom, the stretching rod 23 continues its linear course so as to stretch the tubular body 3*a* of the parison 3 until substantially reaching the desired length of the container to be obtained.

During the actual blowing phase, the stretching rod 23 retracts until it emerges from the moulded container.

All the embodiments described and illustrated herein include the option of completing decontamination of the internal walls of the moulded container by blowing more plasma inside the latter once moulding by blowing and stretching has been completed. Upon completion of the moulding process, the residual gas remaining inside the container passes through the blowing nozzle (6) and is evacuated through a discharge line (unillustrated) controlled by the valve unit.

The characteristics and the advantages of the moulding device for moulding a container starting with a parison in plastic material according to the present invention prove to be clearly indicated in the description provided.

In particular, by generating the plasma at a pressure higher than the atmospheric pressure and using it as a substitution for the blowing fluid, the parison can be moulded and decontaminated at the same time.

The proposed moulding device is compact and structurally simple, in that it requires the sole presence of a plasma generator, in addition to the normal elements already present in a moulding device for moulding by blowing and stretching (compressor, valve unit, mould, stretching rod, blowing nozzle, etc.).

Given that sterilisation and moulding of the parison are inseparable processes, no further measures are required to maintain ambient contamination below the desired level. In fact, the container is moulded under sterile conditions owing to the plasma blown into it. Therefore, the dimensions are limited and the line is simplified in light of the simultaneous execution of the decontamination and moulding processes, which until now had always been performed sequentially.

The structural complexity of the "aseptic" blower with an isolator can thus be left aside, along with all the members operating at the interface thereof (e.g. sealing systems between the sterile zone and the external environment, confinement of the stretching rod, sterilisation system for the blown air circuit, etc.).

A "conventional" blower can be employed, given that the sterilisation process is carried out in the blowing cavity, at the same time as the blowing process and/or subsequently on the moulded container (prior to reopening the mould). This "conventional" blower thus becomes a blower-steriliser.

Sterilisation cycles for sterilising the environment and the blown air prior to production are no longer necessary. The steriliser for sterilising the parisons upstream of the blower can thus be eliminated.

Moreover, the use of plasma makes it possible to reduce sterilisation time, to avoid the use of chemical agents and the accumulation of peroxides in the container and to decontaminate the parison and the container in a substantially uniform manner.

In the first embodiment, by positioning the plasma generator near the blowing nozzle greater efficiency is also achieved due to the reduction of the pathway for radical species (commonly known by the acronym R.O.S. for "Reactive Oxygen Species") present in the plasma, which are short-lived.

Again, in the first embodiment, the incorporation of the plasma generator in the valve unit makes for an even more compact solution.

The first embodiment further comprises the discharge line in parallel with the plasma generator so as to prevent drops in pressure due to evacuation of the residual gas to the plasma generator.

In the preferred variant of the second embodiment, the plasma generator operates with relatively low inlet pressures (maximum 8 bar, approximately), which further simplifies the overall structural design.

In conclusion, owing to the fact that the blowing nozzle creates a tight seal on the bague, the plasma also flows over the external surface of the neck of the parison and thus decontaminates it.

The invention claimed is:

1. Moulding device (1) of a container (2) starting with a parison (3) in plastic material, comprising:
   two half-moulds (4a, 4b) which may be joined to define at least one housing cavity (5) of the parison (3);
   supply means (7) of a blowing fluid having a pressure higher than the atmospheric pressure;
   a blowing nozzle (6) applicable on the neck (3b) of said parison (3); and
   a plasma generator (8) having an inlet (9) receiving the blowing fluid from said supply means (7) and an outlet (10) enabled to supply plasma at pressure higher than the atmospheric pressure to said blowing nozzle (6), so that said plasma is blown into the parison (3) placed in said housing cavity (5) to mould it at least partially and to decontaminate it;
   wherein said supply means (7) of the fluid comprises:
   at least one compression stage (16) of the fluid enabled to generate said blowing fluid, said at least one compression stage (16) being placed upstream of the plasma generator (8);
   a plasma distribution circuit which receives the plasma from the outlet (10) of the plasma generator (8), said distribution circuit including a primary line enabled to transport plasma at a maximum pressure of around 16 bar and a secondary line enabled to transport plasma at a maximum pressure of around 40 bar; and
   a valve unit configured to place in selective communication said primary line and said secondary line with the blowing nozzle (6).

2. Moulding device (1) according to claim 1, wherein said at least one compression stage (16) generates a blowing fluid with a maximum pressure of around 40 bar.

3. Moulding device (1) according to claim 1, wherein said plasma generator (8) is a plasma torch provided with a mobile plug to allow generation of the plasma independently of the pressure value of the blowing fluid at the inlet (9).

4. Moulding device (1) according to claim 1, wherein said at least one compression stage (16) generates blowing fluid having a maximum pressure of around 8 bar, said moulding device (1) further comprising one or more compression stages (21, 22) of the plasma enabled to compress the plasma coming from said outlet (10) of the plasma generator (8) up to a maximum pressure of around 40 bar.

5. Moulding machine of containers (2) starting from parisons (3) in plastic material, comprising a plurality of moulding devices (1) according to claim 1.

* * * * *